United States Patent [19]

Kim

[11] Patent Number: 5,658,288

[45] Date of Patent: Aug. 19, 1997

[54] UNIVERSAL DYNAMIC COMPRESSION DEVICE FOR INTRAMEDULLARY SYSTEM

[76] Inventor: Andrew C. Kim, 30213 Del Rey Rd., Temecula, Calif. 92591

[21] Appl. No.: 618,366

[22] Filed: Mar. 19, 1996

[51] Int. Cl.⁶ ............................................. A61B 17/72
[52] U.S. Cl. ...................................... 606/64; 606/73
[58] Field of Search .............................. 606/62, 63, 64, 606/65, 66, 67, 68, 72, 73, 105, 69, 70, 71

[56] References Cited

U.S. PATENT DOCUMENTS

| | | | |
|---|---|---|---|
| 2,821,979 | 2/1958 | Cameron | 606/64 |
| 4,875,475 | 10/1989 | Comte et al. | 606/64 |
| 5,458,600 | 10/1995 | Stapert et al. | 606/63 |

Primary Examiner—Michael Buiz
Assistant Examiner—David O. Reip
Attorney, Agent, or Firm—Baker, Maxham, Jester & Meador

[57] ABSTRACT

A compression interlocking system for stabilizing long bone fractures, comprises an elongated intramedullary rod having a proximal end, a distal end and a longitudinal axis, the rod adapted for extending within a bore generally parallel to a longitudinal axis of a long bone from a proximal end of the bone to beyond a fracture of the bone, a threaded member for fixing the proximal end of the rod to a first portion of a bone having a fracture, a second member for fixing the distal end to a second portion of the bone having the fracture, and a cam for moving the second portion of the bone toward the first portion of the bone for closing and applying compression to the fracture.

13 Claims, 3 Drawing Sheets

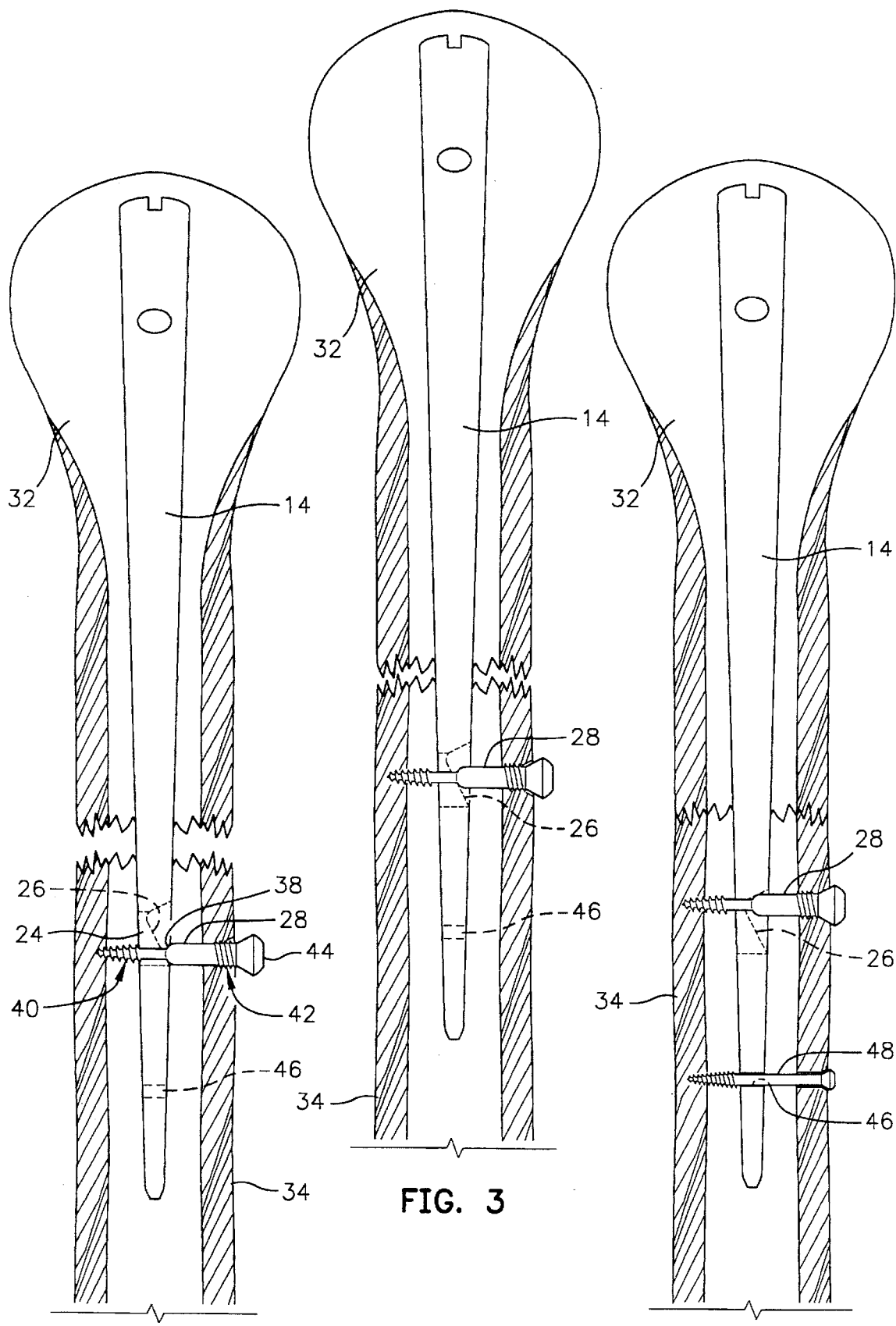

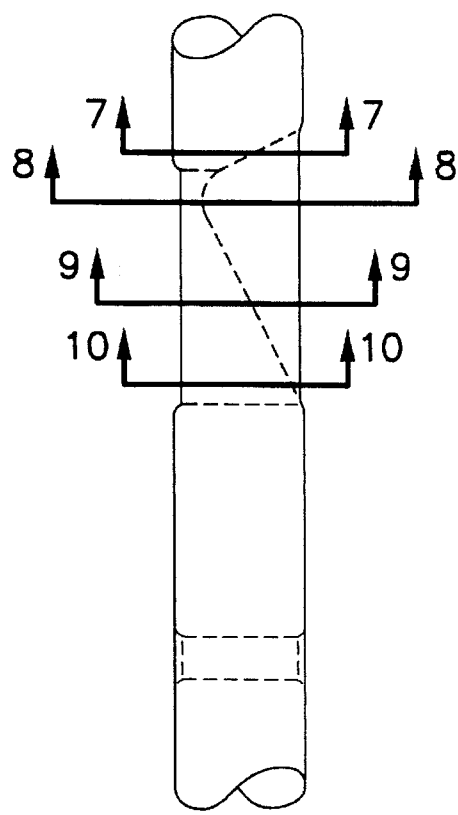
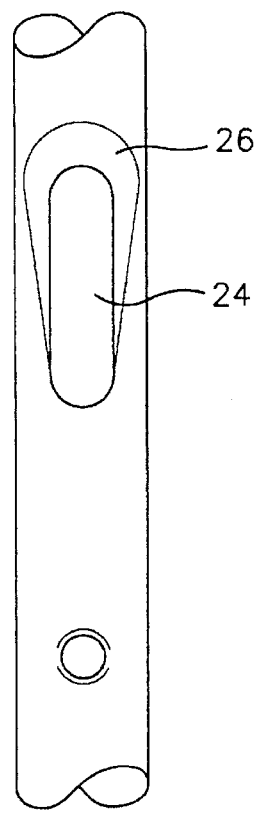
FIG. 5  FIG. 6
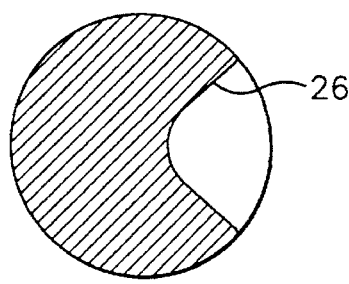
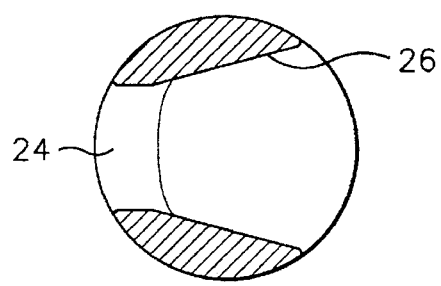
FIG. 7  FIG. 8
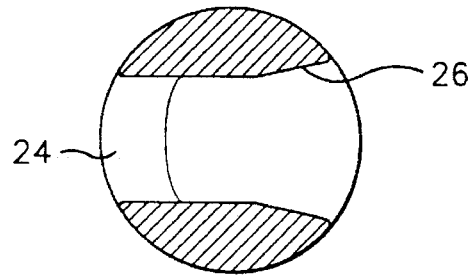
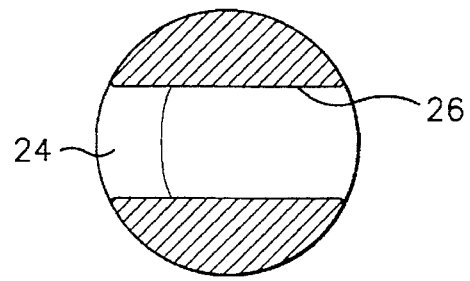
FIG. 9  FIG. 10

UNIVERSAL DYNAMIC COMPRESSION DEVICE FOR INTRAMEDULLARY SYSTEM

BACKGROUND OF THE INVENTION

The present invention relates to medical devices and pertains particularly to an improved rod fixation system for fractures in long bones.

Fractures in long bones in the human body can properly heal only if the two portions of the fractured bones are properly positioned and fixed relative to each other. Such fractures are frequently assisted in their mending by utilizing either an external or internal splint. Internal splints are preferred for most fractures and consist of an elongated intramedullary rod or nail inserted in a bore extending along the axis of the bone and secured by screws to tie the two parts of the fractured bone together until healing can occur. A major difficulty with prior art devices in the case of humerus is that non-union or delayed union frequently occurs. I have found that part of the reason is that the applied force is tensile force rather than compression required to force the two parts of the fractured bone together to enable mending.

In my prior patent, U.S. Pat. No. 5,480,402, entitled "Shoulder Compression Interlocking System", I disclosed an improved rod and interlocking system which improved the stabilization of bone fractures. However, that structure was unable to apply the necessary compressive forces discovered to be necessary.

In fracture healing, there are two basic requirements: osteoconduction and osteoinduction. Osteoconduction is a physical, mechanical requirement. Contact or continuity of bone ends is important for fracture healing. Osteoinduction is the consideration of biological biomechanical induction of bone healing and bone formation. Blood circulation, soft tissue preservation, Wolf's law are important considerations for osteoinduction.

Nonsurgical treatment with cast application stresses osteoinduction aspect in fracture healing. Surgical fixation, such as plate fixation stresses more of the osteoconduction aspect. In this method, a small gap in the fracture fixation can be very harmful with danger of nonunion developing. Successful healing of the callus tissue is affected by the stress it received (Perren). Stress is a function of the following factors:

$$\text{Stress} \propto \frac{\Delta l}{l}$$

Δl=motion in the gap
l=width of the gap

Therefore, a small gap in internally fixed fracture imposes greater danger of developing nonunion than a nonoperative fracture with a larger gap. Under such circumstances, there is already less reliance on osteoinduction and the benefit of osteoconduction is compromised by micromotion significant in proportion to the size of the gap.

Intramedullary rod fixation without interlocking provides internal splint effect. It gives closer reduction to provide better anatomical alignment and osteoconduction effect. Weight bearing allows compression of fracture site narrowing gaps. The rod still allows transfer of Wolf's stress and osteoinduction. However, intramedullary rod system does not provide torsional stability. Therefore interlocking intramedullary fixation system was devised to compensate for torsional stability or to prevent excessive shortening when a comminuted fracture did not provide cortical stability.

Interlocking intramedullary rod systems are currently widely used. As a result, the interlocking system, though it may provide rotational stability, usually creates fixed gap at the fracture site. The gap bypasses the stress from the bone to the implant sometimes causing implant failure such as screw or rod breakage. Delayed union is the frequent result.

Interlocking rod fixation does not completely eliminate micro motion due to an oscillating or windshield wiper effect. To eliminate the windshield wiper effect, some manufacturers made two plane interlocking in the distal tibia. The two plane interlocking requires more soft tissue disturbance and increases risks of injury.

A more ideal system would be an interlocking rod with minimal micromotion but with compression or elimination of any gap. The benefits of my new invention in comparison can be summarized as follows:

1) Narrows the fracture gap to the point of contact providing osteoconduction.
2) Eliminates micromotion.
3) Provides dynamic compression at the fracture site, and therefore, osteoinduction through Wolf's stress.
4) Shares the stress through the fractured long bone between the bone and the implant rather than having the implant take up the entire stress. As a result, implant failure such as rod or screw breakage will be minimized.
5) Reduces motion at the distal interlocking (windshield wiper motion) by internal locking of the rod with this newly designed compression screw. Therefore, with one plane approach it achieves the benefit of two plane stability.

There is a need for an improved intramedullary system for providing compression to the fracture site to help bring about faster healing with less implant failure.

It is therefore desirable to have a long bone fixation device that is simple and more effective than present systems.

SUMMARY OF THE INVENTION

It is therefore a primary object of the present invention to provide a more effective long bone fixation device.

In accordance with a primary object of the present invention, a long bone fixation device wherein interlocking screws of rod screw combination have a stepped diameter with a semi-spherical shoulder at the juncture of the two diameters for to more effectively apply compression to the fracture site to enhance healing.

BRIEF DESCRIPTION OF THE PREFERRED EMBODIMENTS

The above and other objects and advantages of the present invention will become apparent from the following description when read in conjunction with the accompanying drawings wherein:

FIG. 2 is a side elevation view of the embodiment of FIG. 1 showing the invention in a first stage of applying compression to a fracture;

FIG. 3 is a view like FIG. 2 showing the invention in a second stage of applying compression to a fracture;

FIG. 4 is a view like FIG. 2 showing the invention in a final stage of applying compression to a fracture;

FIG. 5 is an enlarged partial side elevation view of the cam area of the rod;

FIG. 6 is an enlarged partial front elevation view of the cam area of the rod;

FIG. 7 is a section view taken generally along line 7—7 of FIG. 5;

FIG. 8 is a section view taken generally along line 8—8 of FIG. 5;

FIG. 9 is a section view taken generally along line 9—9 of FIG. 5;

FIG. 10 is a section view taken generally along line 10—10 of FIG. 5;

DETAILED DESCRIPTION OF THE PREFERRED EMBODIMENTS

Figure 1:
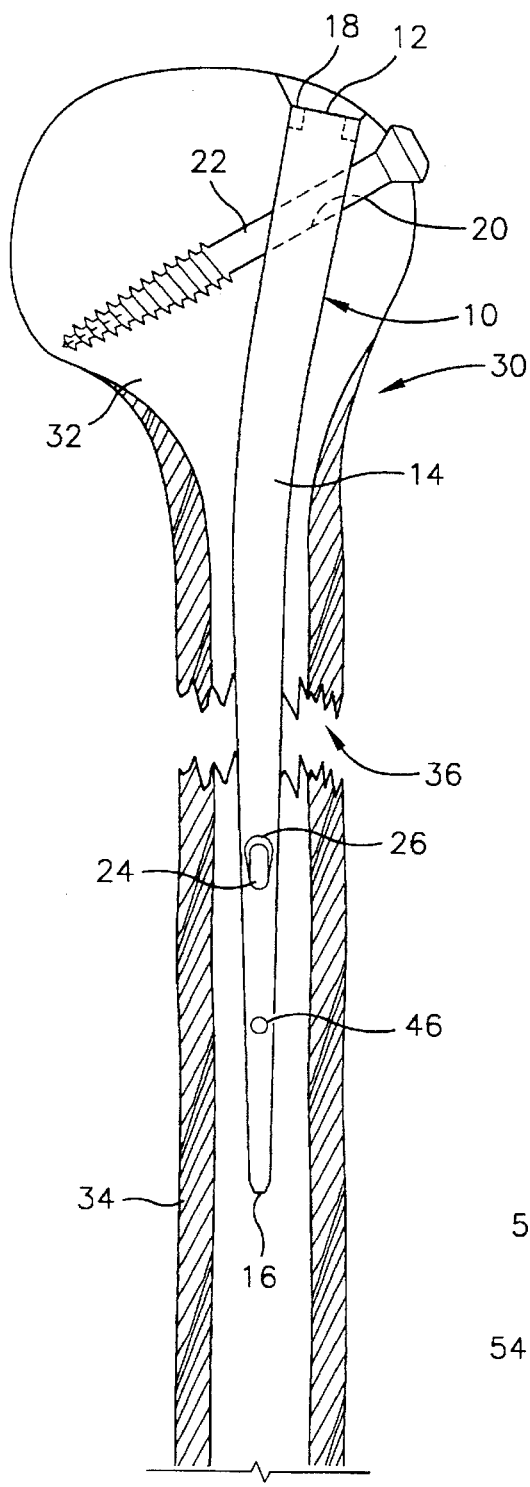
FIG. 1 is a front elevation view of an exemplary preferred embodiment of the invention shown in position for use.

The present invention is directed to an improved intramedullary rod fixation system for long bones for fixation of bones that have been fractured. Referring specifically to FIG. 1 of the drawings there is illustrated a front elevation view in section of a bone having an exemplary embodiment of the rod designated generally by the numeral 10, in accordance with the invention positioned therein. The rod (sometimes called pin or nail in the art) comprises an elongated unitary or integral hollow body having a head or proximal end 12 an elongated intermediate body portion 14 and a distal tip 16. The head end 12 may be formed by a suitable threaded bore and is provided with alignment lugs 18. These lugs are used in conjunction with a guide fixture for alignment for drilling and insertion of lag screws as is known in the art. The rod 10 is provided with one or more transverse screw receiving bores 20 near the proximal end for receipt of fixation lag screws 22. It may be similarly provided with one or more similar bores near the distal tip so as to be positioned beyond the fracture which it is to fix.

An oblong transverse bore 24 is formed in an intermediate position of the shank of the rod 14 at a position to be beyond a fracture in a bone in which the rod is mounted. Surrounding the bore or hole 24 is a cam 26 which cooperates with a shoulder on a specially constructed lag screw 28 for applying compression to a fracture between two portions of a fractured bone. The cam 26 is formed by a sloping surface surrounding the hold or bore 24. The rod, as illustrated in FIG. 1 is inserted into a longitudinally extending bore formed along the center axis of a long bone designated generally by the numeral 30. The bone, as illustrated, has an upper portion 32 and a lower portion 34 which has been fractured from the upper portion along a fracture 36. In the illustrated embodiment the rod 14 has been inserted along the bone in a conventional fashion. The present invention is designed to be utilized in any long bone of the body, such as the humerus, femur, tibia and other bones. The rod preferably has a cannula or elongated longitudinal bore to enable the use of a guide wire (not shown) in a conventional fashion.

Referring to FIG. 2 of the drawing a side elevation view in section of the embodiment of FIG. 1 showing the compression mechanism of the present invention is illustrated. As illustrated, the bore 24 extends across the bore and is oblong or has a somewhat oval configuration defining a somewhat slot like structure extending along the longitudinal axis of the rod 14. Surrounding the rod is a sloping cam shoulder 26 which forms a wedge-like cam sloping inward in the longitudinally upward direction, or toward the head of the rod or pin. This shoulder cooperates with a shoulder 38 on the stepped diameter lag screw 28 between a smaller diameter portion 40 at the distal end and a larger diameter portion 43 near the head 44 of the lag screw. The forward or distal end of the lag screw 28 is formed with self-tapping threads to aid in threading the screw into the bone portion 34. The lag screw is also formed with self-tapping threads on the larger portion 42 at the head and preferably with a non-threaded portion adjacent the shoulder on the head side. The head 44 is preferably formed with apex socket for engagement with an Allan wrench.

In operation, once the rod 14 has been inserted into a bone 30, as shown in FIG. 1, a typical guide instrument is utilized to align a suitable drill with bores at the upper end of the rod, such as bore 20 to enable the drilling of holes for insertion of lag screw 22. Additional screws may be utilized in the arrangement, shown for example in my prior patent, identified above. Once the rod is anchored in the upper portion 32 of the bone 30 the lower bone is properly positioned and properly oriented. The guide fixture is then utilized to locate and drill a hole in the bone portion intersecting the bore 24, as shown in FIG. 2. Preferably the hole through the bone will intercept the oblong bore 24 at its lower most end so that when screw 28 is inserted, ample room for biasing and movement of the bone and screw upward to establish compression in the fracture will be provided. As will be appreciated, the screw 28 having a step diameter, a first drill for portion 40 will be drilled through the bone in alignment with the lower most end of bore 24. Thereafter, a larger hole will be made up to the edge of the rod 14. A preferred method is the utilization of a cannulated or hollow second diameter bore drill that fits over the first drill utilizing the first drill as a guide to maintain precise alignment.

Once the hole is made into the bone, the screw 28 is inserted through hole 24 and threaded into the far side of the bone. As the screw threads into the bone, the shoulder 38 of screw 28 engages and biases against cam surface 26. As the screw 28 moves further inward, it rides upward on the slope 26 carrying the bone portion 34 there along to further move the bones closer together in the area of the fracture 34, as shown in FIG. 3. The screw 28 is threaded in until the lower bone portion moves into engagement with the upper portion 14 and a suitable compression is established. In the ideal position, a suitable compression is reached as the screw approaches or nears the bottom of the slope of the cam 26, as shown in FIG. 4.

The rod 14 may have a curved configuration, as illustrated, or may have a straight configuration depending on its application. The dimensions of the rod including length, diameter, number and position of holes may also vary, depending on the requirements.

Figure 11:
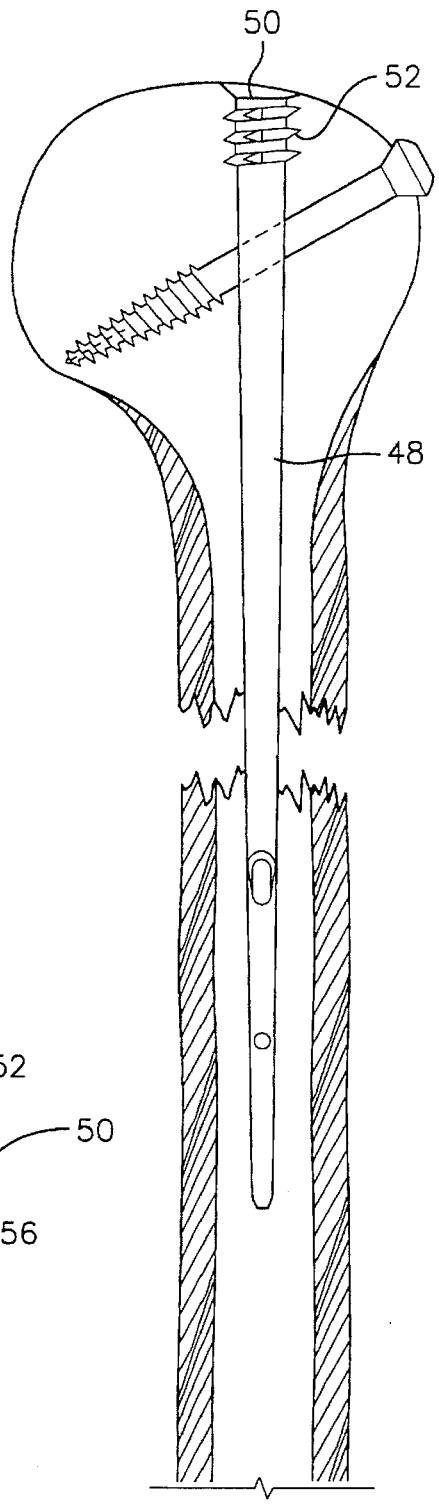
FIG. 11 is a view like FIG. 1 of an alternate embodiment of the invention.

Referring to FIG. 11, further embodiment is illustrated showing a straight rod 48 and utilizing a fixation thread 52 at the top or head 50, as illustrated. The straight rod can be rotated to fix it in the bone by threads 52, which are preferably self-tapping. Additional bores may be provided in the rod in any number of positions and angles, such as disclosed in my prior patent. The additional bores may be positioned to receive conventional lag screws to more securely fix the bone portions to the rod.

Figure 12:
FIG. 12 is a side elevation view of an alternate embodiment of a lag screw.

Referring to FIG. 12, an alternate embodiment of a compression lag screw designated generally by the numeral 50 is illustrated. The screw has a reduced diameter threaded forward portion 52 and an enlarged threaded rear portion 54. A bearing shoulder 56 is formed by a spherical portion 58 intermediate the two different diameter portions of the lag screw. This construction may be preferred in many applications.

While I have illustrated and described my invention by means of specific embodiments, it is to be understood that numerous changes and modifications may be made therein without departing from the spirit and the scope of the invention as defined in the appended claims.

I claim:

1. A compression interlocking system for stabilizing long bone fractures, comprising:

elongated intramedullary rod means having a proximal end, a distal end and a longitudinal axis, said rod means adapted for extending within a bore generally parallel to a longitudinal axis of a long bone from a proximal end of the bone to beyond a fracture of the bone;

first means for fixing said proximal end to a first portion of a bone having a fracture;

second means for fixing said distal end to a second portion of the bone having the fracture; and compression means associated with said second means for moving said second portion of the bone toward said first portion of the bone for applying compression to the fracture, said compression means comprising a cam on said rod and a lag screw having shoulder means for engaging said cam.

2. A system according to claim 1 wherein said second means comprises a transverse bore in said rod, and a lag screw for extending through said bore and anchoring in said second portion of said bone.

3. A system according to claim 1 wherein said cam comprises a sloping surface surrounding said bore in said rod.

4. A system according to claim 3 wherein said bore is elongated slot-like for enabling said screw and said bone portion to move longitudinally of said rod.

5. A system according to claim 1 wherein said second means comprises a transverse bore in said rod, said bore having an elongated diameter longitudinally of said rod, and a lag screw for extending through said bore and anchoring to said bone portion.

6. A system according to claim 5 wherein said compression means comprises a cam on said rod and said lag screw having rounded shoulder means for engaging said cam.

7. A system according to claim 6 wherein said cam comprises an elongated sloping surface surrounding said elongated bore in said rod.

8. A system according to claim 6 wherein said first means for fixing said proximal end comprises self-tapping threads on said proximal end.

9. A system according to claim 1 wherein said first means for fixing said proximal end comprises self-tapping threads on said proximal end.

10. A compression interlocking system for stabilizing long bone fractures, comprising:

elongated intramedullary rod means having a proximal end, a distal end and a longitudinal axis, said rod means adapted for extending within a bore generally parallel to a longitudinal axis of a long bone from a proximal end of the bone to beyond a fracture of the bone;

proximal fixing means for fixing said proximal end to a first portion of a bone having a fracture;

a transverse bore in the rod means for positioning in a second portion of the bone at a position beyond the fracture from said proximal end, said transverse bore having a predetermined diameter and a configuration enabling a lag screw to move longitudinally of the rod when viewing in elevation view of the rod means;

cam means on said rod adjacent said bore for enabling camming a lag screw along said axis of said rod means so that said lag screw may be moved relative to said rod; and a stepped diameter lag screw for extending across said second portion and through said transverse bore, said lag screw having a stepped diameter with a forward end having a diameter less than said predetermined diameter and a rear end greater than said predetermined diameter, and a shoulder between said diameters for engaging said cam means on said rod.

11. A system according to claim 10 wherein said bore has an elongated diameter disposed longitudinally of said rod, and said cam comprises an elongated sloping surface surrounding said elongated bore, said lag screw having rounded shoulder means for engaging said cam.

12. A system according to claim 11 wherein said proximal fixing means for fixing said proximal end comprises self-tapping threads on said proximal end.

13. A system according to claim 10 wherein said proximal fixing means for fixing said proximal end comprises self-tapping threads on said proximal end.

* * * * *